United States Patent [19]

Kraus et al.

[11] Patent Number: 5,434,267
[45] Date of Patent: Jul. 18, 1995

[54] PROCESS FOR THE PREPARATION OF SUBSTITUTED 3-ALKOXYACRYLATES

[75] Inventors: Helmut Kraus, Cologne; Alexander Klausener, Stolberg; Hans-Joachim Diehr, Wuppertal-Vohwinkel, all of Germany

[73] Assignee: Bayer Aktiengesellschaft, Leverkusen, Germany

[21] Appl. No.: 212,335

[22] Filed: Mar. 14, 1994

Related U.S. Application Data

[63] Continuation of Ser. No. 988,570, Dec. 10, 1992, abandoned.

[30] Foreign Application Priority Data

Dec. 20, 1991 [DE] Germany .................. 41 42 191.4

[51] Int. Cl.⁶ .................. C07D 213/64; C07D 213/74; C07D 239/42; C07D 285/08
[52] U.S. Cl. .................. 546/301; 546/302; 546/312; 546/330; 546/335; 546/341; 546/342; 544/182; 544/215; 544/224; 544/239; 544/240; 544/241; 544/318; 544/319; 544/329; 544/335; 544/336; 544/408; 544/409; 548/128; 548/129; 548/136; 548/138; 548/131; 548/132; 548/133; 548/143; 548/144; 548/204; 548/213; 548/214; 548/236; 548/243; 548/245; 548/247; 548/263.2; 548/264.8; 548/268.4; 548/268.6; 548/187; 548/194; 548/341.5; 548/376.1; 548/562; 549/79; 549/501; 560/43; 560/60; 560/120; 560/121; 560/122; 560/123; 560/124; 560/183
[58] Field of Search .................. 544/329, 318, 319, 335; 546/312, 301, 341, 342, 302, 330, 335; 548/128, 129

[56] References Cited

U.S. PATENT DOCUMENTS

| | | |
|---|---|---|
| 3,842,124 | 10/1974 | Felder et al. .................. 562/455 |
| 4,278,808 | 7/1981 | Felder et al. .................. 560/183 |
| 4,515,984 | 5/1985 | El-Chahawi .................. 560/183 |
| 4,968,709 | 11/1990 | Kleefeld et al. .................. 514/370 |
| 5,021,581 | 6/1991 | Clough et al. .................. 560/60 |
| 5,030,747 | 7/1991 | Blank et al. .................. 560/172 |
| 5,036,085 | 7/1991 | Heinemann et al. .................. 514/361 |
| 5,120,734 | 6/1992 | Klausener et al. .................. 514/252 |
| 5,120,755 | 6/1992 | Kleefeld et al. .................. 514/370 |
| 5,124,353 | 6/1992 | Clough et al. .................. 560/60 |
| 5,138,058 | 8/1992 | Geisen et al. .................. 544/295 |
| 5,189,063 | 2/1993 | Klausener et al. .................. 560/15 |

FOREIGN PATENT DOCUMENTS 0383117 8/1990 European Pat. Off. .
0389901 10/1990 European Pat. Off. .

OTHER PUBLICATIONS

Lapkin et al, *Chemical Abstracts*, vol. 65, No. 8753 C (1966).
Jelich et al, *Chemical Abstracts*, vol. 112, No. 76943 (1990) (Abstract for EP 329011, Aug. 23, 1989).

*Primary Examiner*—Emily Bernhardt
*Attorney, Agent, or Firm*—Sprung Horn Kramer & Woods

[57] ABSTRACT

Process for the preparation of compounds of the formula (I)

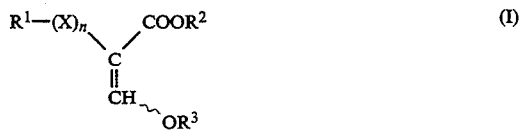

in which $R^1$, $R^2$, $R^3$, X and n have the meaning given in the description, by reacting acetates with carbon monoxide in the presence of a basic auxiliary, followed by alkylation. The products are intermediates for fungicidal acrylates.

6 Claims, No Drawings

PROCESS FOR THE PREPARATION OF SUBSTITUTED 3-ALKOXYACRYLATES

This application is a continuation of application Ser. No. 988,570, filed Dec. 10, 1992, now abandoned.

The invention relates to a new process for the preparation of substituted 3-alkoxyacrylates which can be used as fungicides or as intermediates for the preparation of fungicidal acrylates.

It has been disclosed that certain fungicidally active alkoxyacrylates are obtained when suitable acetate derivatives are subjected to a condensation reaction with formate derivatives in the presence of a base and then the resulting 3-hydroxyacrylate derivatives are alkylated in a second step or, if appropriate, alternatively in a one-pot reaction, directly after the condensation, with alkylating agents on the 3-hydroxyl group in the presence of a base (cf., for example, DE-OS (German Published Specification) 3,805,059; DE-OS (German Published Specification) 3,807,232).

The disadvantage of this process is the fact that the Claisen condensation, which is carried out as the first step, frequently only gives very poor yields and fails completely in the case of some acetate derivatives, depending on the nature of the substituent in the α position relative to the alkoxycarbonyl group. For example, it is especially difficult in some cases to react alkyl [(N-pyridyl-N-alkyl)-amino]-acetate or alkyl [(N-pyrimidyl-N-alkyl)-amino]-acetate in the above-mentioned manner in the first place. Either the process requires strong bases such as, for example, lithium diisopropylamide, potassium hydride or potassium tert.-butanolate, which is disadvantageous ad complicated, in particular with a view to technical aspects because of the hazard problems which this process entails, or the acetate derivatives are first converted into substituted 3-amino-acrylates by reaction with orthoformamidates, and these substituted 3-amino-acrylates are then hydrolysed to give 3-hydroxy acrylates, which are finally converted into the desired 3-alkoxy-acrylates using basic auxiliaries and suitable alkylating agents. In general, this process gives good yields, but is technically complicated and economically disadvantageous because orthoformamidate is used and because an additional reaction step is required.

Furthermore, it has been disclosed that fungicidally active substituted 3-alkoxyacrylates are obtained when suitable acetate derivatives are reacted with formamides or formamide derivatives, the substituted 3-amino-acrylates obtained in this process are hydrolysed to give 3-hydroxy-acrylates, and these are finally converted into the desired 3-alkoxy-acrylates using basic auxiliaries (for example DE-OS (German Published Specification) 3,807,232; DE-OS (German Published Specification) 3,910,358).

However, the dimethylformamide dialkyl acetals used in this process frequently only give very poor yields of the desired intermediate 3-amino-acrylate.

It was therefore an object to find a process which permits the desired 3-alkoxy-acrylates to be synthesised starting from acetate derivatives using agents which are simple from the point of view of production engineering and starting materials which are readily accessible and easy to handle.

It has now been found that substituted 3-alkoxyacrylates of the general formula (I)

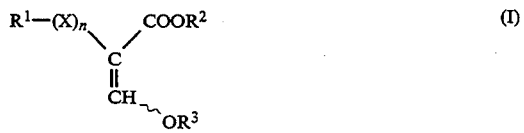

in which
R$^1$ represents an in each case optionally substituted carbo- or heterocycle,
R$^2$ represents optionally substituted alkyl,
R$^3$ represents optionally substituted alkyl and
X represents oxygen, sulphur or one of the radicals

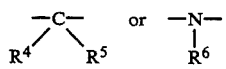

and
n represents a number 0 or 1, where
R$^4$, R$^5$ and R$^6$ independently of one another in each case represent hydrogen or in each case optionally substituted alkyl or alkenyl,
are obtained when substituted acetates of the formula (II)

in which
R$^1$, R$^2$, X and n have the above-mentioned meaning are first reacted with carbon monoxide and a basic auxiliary in the presence of a suitable diluent, and intermediates of the general formula (III)

in which
R$^1$, R$^2$, X and n have the above-mentioned meaning and
M$^⊕$ represents hydrogen or the equivalent of an alkali metal cation or alkaline earth metal cation or ammonium cation (preferably of a sodium or potassium cation),
are obtained in this process, whereupon the free enols are isolated from these salts by acidification with dilute acids such as, for example, dilute hydrochloric acid, followed by extraction with a suitable organic solvent such as, for example, ethyl acetate, and are then alkylated with the alkylating agent in a suitable diluent in the presence of a suitable base at temperatures from 20° C. to 60° C.

Alternatively, it is possible to react the enolate salts of the formula (III) with the alkylating agent directly in the reaction mixture. In a particularly preferred variant of this "one-pot reaction", an excess of the basic auxiliary, for example sodium methylate, is first used during the carbonylation reaction this gives the enolate of the formula (III) in the reaction mixture in the form of the sodium salt, as well as unreacted sodium methylate. This unreacted sodium methylate can be neutralised using a suitable acid such as, for example, methanesulphonic acid, and thereupon the methylating agent is added together with a further equivalent of base such as, for example potassium carbonate.

This procedure dispenses with an excess of methylating agent, which would otherwise be required in order to compensate for losses caused by its reaction with sodium methylate.

Another, particularly preferred variant of this "one-pot reaction" first uses a stoichiometric amount, or a small (about 5 to 35%) excess of the basic auxiliary, for example sodium methylate, during the carbonylation reaction.

This gives the enolate of the formula (III) in the reaction mixture in the form of the sodium salt as well as unreacted sodium methylate in amounts which by now are only very small but correspond to the employed excess of the basic auxiliary. In particular when the sodium methylate to be used can successfully be limited to the stoichiometrically required amount, a scavenging of unreacted basic auxiliary, for example by adding a suitable acid, can be dispensed with, and the alkylating agent can be introduced directly into the reaction mixture. This procedure allows the use of excess alkylating reagent to be limited or, in favourable cases, to be dispensed with completely.

The resulting alkoxymethylene carboxylates of the formula (I) and the enols, or enol salts, of the formula (III) are known in principle (cf. EP 384,211, EP 331,966, EP 383,117) and are potent fungicides.

It is highly surprising that the reaction according to the invention of the acetate derivatives of the general formula (II) with carbon monoxide is successful and unproblematic even in those cases in which the very similar reaction of the starting material with methyl formate in the presence of bases or the reaction with dialkylformamide dialkyl acetals is entirely, or almost completely, unsuccessful, and even the procedure of the reaction with orthoformamidates, which, however, is much more complicated, is only insufficiently successful.

It is therefore a particular advantage of the process according to the invention that its application makes compounds accessible which could previously not be obtained at all, or in very poor yield only, by using a procedure which is simplified compared with the prior art and particularly suitable for carrying out the process in industrial apparatus.

A further advantage of the process according to the invention consists in the fact that the substituted enols, or enol salts, of the general formula (III) which can be obtained in a simple manner and in high yield with the aid of the process according to the invention are outstandingly suitable for the preparation of fungicidal 3-alkoxy-acrylates or else other 3-substituted acrylates, when they are alkylated with the aid of simple, known processes, either directly in a second, separate reaction step or directly afterwards, using a one-pot process, or when consecutive reactions are carried out which are typical for enols or enol salts, equally with the aid of known, simple processes, the following being mentioned by way of example and as being preferred, but not in conclusion:

reaction with amines to give substituted 3-aminoacrylates, reaction with mercaptans to give substituted 3-alkylthio- or 3-arylthio-arcylates or reaction with acid halides to give 3-acyloxy- or 3-sulphonyloxy-acrylates.

Formula (I) provides a general definition of the substituted 3-alkoxyacrylates which can be obtained with the process according to the invention. Compounds of the formula (I) in which $R^1$ represents a saturated, monounsaturated or polyunsaturated or aromatic carbocycle which has 5 to 10 carbon atoms and which is optionally monosubstituted or polysubstituted by identical or different substituents, or represents a saturated, monounsaturated or polyunsaturated or aromatic heterocycle which has 2 to 9 carbon atoms and 1 to 5 identical or different hereto atoms—in particular nitrogen, oxygen or sulphur—and which is optionally monosubstituted or polysubstituted by identical or different substituents, suitable substituents in each case being: halogen, cyano, nitro, in each case straight-chain or branched alkyl, alkoxy or alkylthio, each of which has 1 to 6 carbon atoms, in each case straight-chain or branched halogenoalkyl, halogenoalkoxy or halogenoalkylthio, each of which has 1 to 4 carbon atoms and 1 to 9 identical or different halogen atoms, in each case straight-chain or branched alkoxycarbonyl or alkoximinoalkyl, dialkylamino or dialkylaminocarbonyl, each of which has 1 to 4 carbon atoms in the individual alkyl moieties, in each case straight-chain or branched alkenyl or alkinyl, each of which has 2 to 8 carbon atoms, cycloalkyl having 3 to 7 carbon atoms, divalent alkanediyl having 3 to 5 carbon atoms, or aryl, aryloxy, arylthio, arylcarbonyl, aralkyl aralkenyl, aralkinyl, aralkyloxy, aralkylthio, heteroarylalkyl, heteroarylalkenyl, heteroyryloxy, heteroarylthio, heteroarylcarbonyl, heteroarylalkyloxy, heteroarylalkylthio, or heteroaryl, each of which has 6 to 10 carbon atoms in the aryl moiety or 2 to 9 carbon atoms and i to 4 identical or different hetero atoms—in particular nitrogen, oxygen and/or sulphur—in the heteroaryl moiety and, if appropriate, 1 to 6 carbon atoms in the straight-chain or branched alkyl moiety or, if appropriate, 2 to 6 carbon atoms in the straight-chain or branched alkenyl moiety, or alkinyl moiety, respectively, and each of which is optionally monosubstituted or polysubstituted in the aryl moiety or in the heteroaryl moiety by identical or different substituents from the series comprising halogen, alkylalkoxy, alkylthio, halogenoalkyl, halogenoalkoxy, halogenoalkyl thio, dioxyalkylene, halogen-substituted dioxyalkylene or optionally substituted phenyl;

$R^2$ represents straight-chain or branched alkyl having 1 to 6 carbon atoms, or represents aralkyl which has 1 to 4 carbon atoms in the straight-chain or branched alkyl moiety and 6 to 10 carbon atoms in the aryl moiety and which is optionally monosubstituted or polysubstituted in the aryl moiety by identical or different substituents, suitable aryl substituents being: halogen, cyano, nitro, in each case straight-chain or branched alkyl, alkoxy or alkylthio, each of which has 1 to 4 carbon atoms, in each case straight-chain or branched halogenoalkyl, halogenoalkoxy or halogenoalkylthio, each of which has 1 to 4 carbon atoms and 1 to 9 identical or different halogen atoms, in each case straight-chain or branched alkoxycarbonyl or alkoximinoalkyl, each of which has 1 to 8 carbon atoms in the individual alkyl moieties, cycloalkyl having 3 to 7 carbon atoms, divalent alkanediyl having 3 to 5 carbon atoms, aryl, aralkyl, aryloxy or aralkyloxy, each of which has 6 to 10 carbon atoms in the aryl moiety and, if appropriate, 1 to 4 carbon atoms in the straight-chain or branched alkyl moiety and each of which is optionally monosubstituted or polysubstituted in the aryl moiety by identical or different substituents from the series comprising halogen, alkyl, alkoxy, alkylthio, halogenoalkyl, halogenoalkoxy or halogenoalkylthio, each of which has 1 to 4 carbon atoms and, if appropriate, 1 to 9 identical or different halogen atoms, or heteroarylalkyl or heteroaryl, each of which has 2 to 9 carbon atoms and 1 to 4 identical or different hetero atoms,—in particular nitrogen, oxygen and-/or sulphur—in the heteroaryl moiety and, if appropriate, 1 to 4 carbon atoms in the straight-chain or branched alkyl moiety and each of which is optionally monosubstituted or polysubstituted in the heteroaryl moiety by identical or different substituents from the series comprising halogen, alkyl, alkoxy, alkylthio, halogenoalkyl, halogenoalkoxy or halogenoalkylthio, each of which has 1 to 4 carbon atoms and, if appropriate, 1 to 9 identical or different halogen atoms; $R^3$ represents straight-chain or branched alkyl having 1 to 6 carbon atoms, or represents aralkyl which has 1 to 4 carbon atoms in the straight-chain or branched alkyl moiety and 6 to 10 carbon atoms in the aryl moiety and which is optionally monosubstituted or polysubstituted in the acryl moiety by identical or different substituents, suitable aryl substituents beings: halogen, cyano, nitro, in each case straight-chain or branched alkyl, alkoxy or alkylthio, each of which has 1 to 4 carbon atoms, in each case straight-chain or branched halogenoalkyl, halogenoalkoxy or halogenoalkylthio, each of which has 1 to 4 carbon atoms and 1 to 9 identical or different halogen atoms, in each case straight-chain or branched alkoxycarbonyl or alkoximinoalkyl, each of which has 1 to 8 carbon atoms in the individual alkyl moieties, cycloalkyl having 3 to 7 carbon atoms, divalent alkanediyl having 3 to 5 carbon atoms, aryl, aralkyl, aryloxy or aralkyloxy, each of which has 6 to 10 carbon atoms in the aryl moiety and, if appropriate, 1 to 4 carbon atoms in the straight-chain or branched alkyl moiety and each of which is optionally monosubstituted or polysubstituted in the aryl moiety by identical or different substituents from the series comprising halogen, alkyl, alkoxy, alkylthio, halogenoalkyl, halogenoalkoxy or halogenoalkylthio, each of which has 1 to 4 carbon atoms and, if appropriate, 1 to 9 identical or different halogen atoms, or heteroarylalkyl or heteroaryl, each of which has 2 to 9 carbon atoms and 1 to 4 identical or different hetero atoms,—in particular nitrogen, oxygen and/or sulphur—in the heteroaryl moiety and, if appropriate, 1 to 4 carbon atoms in the straight-chain or branched alkyl moiety and each of which is optionally monosubstituted or polysubstituted in the heteroaryl moiety by identical or different substituents from the series comprising halogen, alkyl, alkoxy, alkylthio, halogenoalkyl, halogenoalkoxy or halogenoalkylthio, each of which has 1 to 4 carbon atoms and, if appropriate, 1 to 9 identical or different halogen atoms;

X represents oxygen, sulphur or one of the radicals

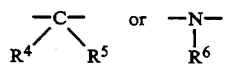

and n represents a number 0 or 1, where $R^4$, $R^5$ and $R^6$ independently of one another in each case represent hydrogen, in each case straight-chain or branched alkyl having 1 to 6 carbon atoms, alkenyl having 2 to 6 carbon atoms, or aralkyl which has 1 to 6 carbon atoms in the straight-chain or branched alkyl moiety and 6 to 10 carbon atoms in the aryl moiety or aralkenyl which has 2 to 6 carbon atoms in the straight-chain or branched alkenyl moiety and 6 to 10 carbon atoms in the aryl moiety, each of which is optionally monosubstituted or polysubstituted in the aryl moiety by identical or different substituents, suitable aryl substituents in each case being those mentioned in the case of $R^2$, can preferably be prepared.

Compounds of the formula (I) in which $R^1$ represents a phenyl radical which is optionally monosubstituted to pentasubstituted by identical or different substituents and/or benzo-fused, or represents a cycloalkenyl radical which is optionally monosubstituted to pentasubstituted by identical or different substituents and which has 5 to 7 carbon atoms, or represents a heteroaryl radical which is optionally monosubstituted to pentasubstituted by identical or different substituents and/or benzo-fused and which has 1 to 5 carbon atoms and 1 to 3 hetero atoms—in particular nitrogen, oxygen or sulphur—, suitable substituents in each case being: fluorine, chlorine, bromine, cyano, nitro, methyl, ethyl, n- or i-propyl, n-, i-, s- or t-butyl, methoxy, ethoxy, n- or i-propoxy, methylthio, trifluoromethyl, trifluoromethoxy, trifluoromethylthio, methoxycarbonyl, ethoxycarbonyl, methoximinomethyl, ethoximinomethyl, methoximinoethyl, ethoximinoethyl, dimethylamino, diethylamino, dimethylcarbamoyl, diethylcarbamoyl, allyl, butenyl or propargyl, cyclopropyl, cyclopentyl, cyclohexyl, 1,3-propanediyl, 1,4-butanediyl, 1,5-pentanediyl, or phenyl, naphthyl, phenoxy, phenylthio, phenylcarbonyl, benzyl, phenylethyl, phenylpropyl, phenylethenyl, benzyloxy, heteroaryloxy, heteroarylmethyl or heteroaryl, each of which is optionally monosubstituted to trisubstituted by identical or different substituents from the series comprising fluorine, chlorine, bromine, methyl, ethyl, n- or i-propyl, n-, i-, s- or t-butyl, methoxy, ethoxy, n- or i-propoxy, methylthio, ethylthio, trifluoromethyl, trifluoromethoxy, trifluoromethylthio, dioxymethylene or phenyl which is optionally monosubstituted to trisubstituted by identical or different substituents from the series comprising fluorine, chlorine, methyl, methoxy or trifluoromethyl, suitable individual heteroaryl radicals in each case being the following:

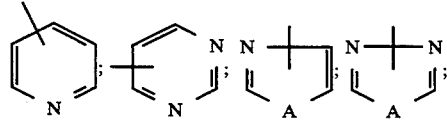

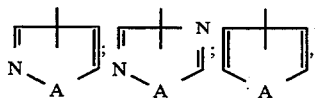

which can optionally also be benzo-fused and in which

A in each case represents oxygen, sulphur, an NH or an NCH₃ group;

R² represents methyl, ethyl, n- or i-propyl, n-, i-, s- or t-butyl, or represents benzyl which is optionally monosubstituted to trisubstituted by identical or different substituents, suitable substituents being: fluorine, chlorine, bromine, cyano, nitro, methyl, ethyl, n- or i-propyl, n-, i-, s- or t-butyl, methoxy, ethoxy, n- or i-propoxy, methylthio, trifluoromethyl, trifluoromethoxy, difluoromethoxy, trifluoromethylthio, methoxycarbonyl, ethoxycarbonyl, methoximinomethyl, ethoximinomethyl, methoximinoethyl, ethoximinoethyl, cyclopentyl, cyclohexyl 1,3-propanediyl, 1,4-butanediyl, or phenyl, benzyl, phenoxy or benzyloxy, each of which is optionally monosubstituted to trisubstituted in the phenyl moiety by identical or different substituents from the series comprising fluorine, chlorine, bromine, methyl, ethyl, methoxy, ethoxy, methylthio, trifluoromethyl, difluoromethoxy, trifluoromethoxy and/or trifluoromethylthio, R³ represents methyl, ethyl, n- or i-propyl, or n-, i-, s- or t-butyl, X represents oxygen, sulphur or one of the radicals

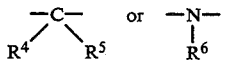

and n represents a number 0 or 1, where

R⁴, R⁵ and R⁶ independently of one another in each case represent hydrogen, methyl, ethyl, n- or i-propyl, n-, i-, s- or t-butyl, or benzyl or phenyl, each of which is optically monosubstituted to trisubstituted by identical or different substituents, suitable substituents in each case being those mentioned in the case of R², can particularly preferably be prepared.

Compounds of the general formula (I) in which

R¹ represents a phenyl radical which is optionally monosubstituted to trisubstituted and/or benzo-fused, a cyclohexenyl radical or cyclopentenyl radical, each of which is optionally monosubstituted to trisubstituted by identical or different substituents and/or benzo-fused, or a heteroaryl radical which is optionally monosubstituted to trisubstituted and/or benzo-fused, particularly suitable heteroaryl radicals beings:

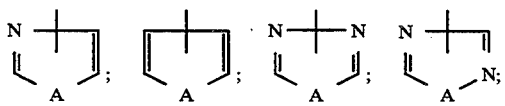

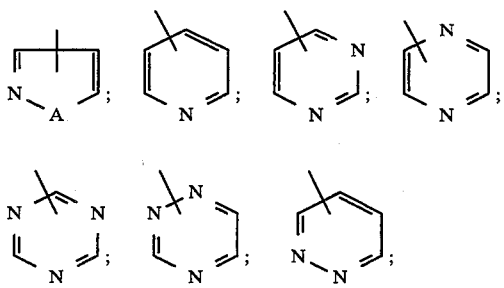

where

A in each case represents oxygen, sulphur, an NH or an N—CH₃ group, and suitable phenyl, cyclopentenyl, cyclohexenyl or heteroaryl substituents in each case being: fluorine, chlorine, bromine, cyano, nitro, methyl, ethyl, methoxy, methylthio, trifluoromethyl, trifluoromethoxy, trifluoromethylthio, methoxycarbonyl, ethoxycarbonyl or dimethylamino, or in each case optionally once to three times, identical or different, by fluorine, chlorine, methyl, ethyl, methoxy, trifluoromethyl, dioxyethylene or phenyl, phenoxy, phenylcarbonyl, benzyl, pyridyl, pyrazolyl, oxazolyl, thiazolyl, thienyl, furyl, thiadiazolyl, oxadiazolyl, imidazolyl or triazolyl, R² represents methyl, ethyl, n- or i-propyl or benzyl, R² represents methyl, ethyl, n- or i-propyl or benzyl, R³ represents methyl, ethyl, n- or i-propyl or benzyl, X represents oxygen, sulphur or one of the radicals

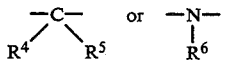

and n represents a number 0 or 1, where

R⁴, R⁵ and R⁶ independently of one another in each case represent hydrogen, methyl, ethyl, n- or i-propyl or benzyl, can very particularly preferably be prepared.

Aryl as such or in combinations preferably denotes phenyl or naphthyl, in particular phenyl.

All aliphatic radicals as such or in combintions are straight-chain or branched.

Unless otherwise defined, halogen represents fluorine, chlorine, bromine or iodine, in particular fluorine, chlorine or bromine.

If, for example, methyl N-methyl-N-[2-(6-phenyl)-pyridyl]-glycinate is used as starting material, the course of the process according to the invention can be represented by the following equation:

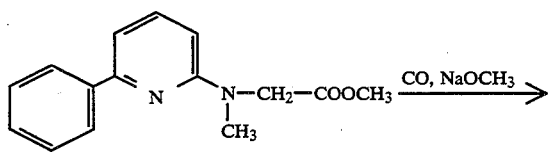

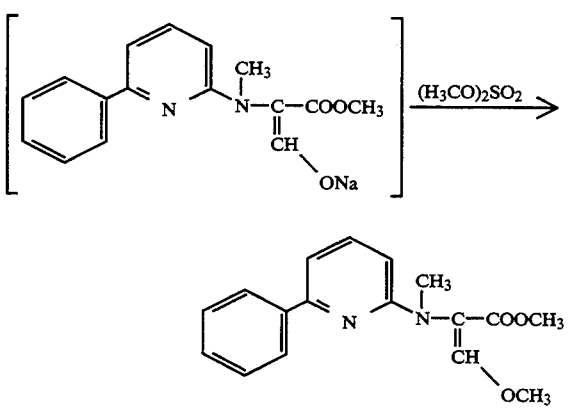

Formula (II) provides a general definition of the substituted acetates required as starting materials for carrying out the process according to the invention. In this formula (II), $R^1$, $R^2$, X and n preferably represent those radicals which have already been mentioned in connection with the description of the substances of the formula (I) according to the invention as being preferred for these substituents.

The substituted acetates of the formula (II) are known or can be obtained in analogy to known processes (cf., for example, J. Chem. Pharm. Bull. 23, 3008–3010 [1975]; Prakt. Chem. 315, 1175–1182 [1973]; Chimia 28, 235–236 [1974]; Pak. J. Sci. Ind. Res. 20, 139–149 [1977]; J. Heterocycl. Chem. 5, 281–283 [1968]; Pol. J. Chem. 53, 2349–2354 [1979]; J. Heterocycl. Chem. 24, 85–89 [1987]; Zh. org. Khim. 20, 1517–1538 [1984]; Zh. Org. Khim. 20, 2002–2011 [1984]; Izv. Akad. Nauk SSSR. Set. Khim. 1984, 2760–2765; DE 2,103,728; DE 2,637,911; DE 2,709,108; DE 2,725,361; DE 2,425,282; GB 1,161,492 [1969]; EP 182,769; EP 245,230; EP 227,932; DE-OS (German Published Specification) 3,904,931; DE-OS (German Published Specification) 3,805,059; DE-OS (German Published Specification) 3,807,232; DE-OS (German Published Specification) 3,905,119; DE-OS (German Published Specification) 3,904,931).

Basic auxiliaries which are suitable are all inorganic and organic bases which can customarily be used and which are active under the reaction conditions. The following are preferably used: alkali metal hydrides, alkali metal hydroxides, alkali metal amides or alkali metal alcoholates such as, for example, sodium hydride, sodium amide, sodium hydroxide, sodium methylate, sodium methylate or potassium t-butylate, the use of sodium methylate, sodium ethylate and potassium t-butylate is particularly preferred.

Suitable diluents for carrying out the first step, or the first part-step, of the process according to the invention are mainly inert organic solvents. These include, in particular, aliphatic, alicyclic or aromatic, optionally also halogenated hydrocarbons such as, for example, benzine, benzene, toluene, xylene, chlorobenzene, petroleum ether, hexane, cyclohexane, dichloromethane, chloroform, carbon tetrachloride, ethers, such as diethyl ether, dioxane, tetrahydrofuran or ethylene glycol dimethyl ether or ethylene glycol diethyl ether, amides, such as dimethylformamide, dimethylacetamide, N-methylformanilide, N-methylpyrrolidone or hexamethylphosphoric. triamide.

It is furthermore possible to use alcohols of the general formula $R^2$-OH where the radical $R^2$ should be identical to the radical described in the general formula (I), (II) and (III), to avoid the formation of product mixtures caused by transesterification reactions which are possible under the reaction conditions.

However, it is also possible to employ mixtures of the above-mentioned solvents.

Suitable diluents for carrying out the second step, or the second part-step, of the process according to the invention are the same solvents as those for carrying out the first step, or the first part-step, respectively. In this context, it may be expedient to use a different solvent for the second step, or the second part-step, than for the first step, or the first part-step, respectively.

If appropriate, it may furthermore be advantageous to evaporate the reaction mixture to dryness under reduced or increased pressure or under atmospheric pressure after carrying out the first part-step, or the first step, of the process according to the invention, then, if appropriate, to isolate the intermediate of the general formula (III), preferably in the form of the enol salt, for example by filtration under reduced or increased pressure or under atmospheric pressure, and, if appropriate after intermediate purification, for example by washing or extracting with a suitable organic solvent, to dissolve or disperse the resulting solid in one of the above-described diluents, and then to carry out the second step, or the second part-step, respectively, of the reaction according to the invention.

If the alkylating agent employed for carrying out the second step, or the second part-step, of the process according to the invention is liquid under the reaction conditions, it may be possible, if appropriate, to dispense completely with an addition of a diluent.

When carrying out the process according to the invention, the reaction temperatures can be varied within a substantial range.

In general, the first part-step, or the first step, of the process according to the invention is carried out at temperatures between 0° C. and 200° C., preferably 20° C. and 150° C., and the second part-step, or the second step, respectively, of the process according to the invention is carried out at temperatures between −80° C. and 100° C., preferably −40° C. and 70° C.

The first step, or the first part-step, of the process according to the invention is carried out under increased pressure.

The CO partial pressure is between 1 bar and 200 bar, preferably between 5 bar and 150 bar, particularly preferably between 10 bar and 70 bar. The total pressure is between 5 bar and 200 bar, preferably between 10 bar and 150 bar, particularly preferably between 10 bar and 70 bar. The difference between total pressure and CO partial pressure can be applied by injecting an inert gas, for example nitrogen or argon.

The second step, or the second part-step, of the process according to the invention can be carried out under reduced or increased pressure, but preferably under atmospheric pressure.

When carrying out the second step, or the second part-step, of the process according to the invention, the use of an inert gas atmosphere such as, for example, nitrogen or argon may, if appropriate, be expedient, but in general it is possible to carry out this part-step, or this step, of the process according to the invention under a normal ambient atmosphere.

For carrying out the first part-step, or the first step, of the process according to the invention, 1.0 to 15.0 mol, preferably 1.0 to 5.0 mol, of basic auxiliaries are generally employed per mole of substituted acetates of the formula (II).

The reaction is carried out and the reaction products are worked up and, if appropriate, isolated by generally customary methods (compare also the preparation examples).

For carrying out the second part-step, or the second step, of the process according to the invention, 1.0 to 10.0 mol, preferably 1.0 to 2.0 mol, of basic auxiliaries and 1.0 to 20.0 mol, preferably 1.0 to 5.0 mol, of alkylating reagent are employed per mole of substituted acetates of the general formula (II), or per mole of enols of the general formula (III), which have or have not been subjected to intermediate isolation.

The reaction is carried out and the reaction products are worked up and isolated by generally customary methods (compare also the preparation examples).

EXAMPLE 1

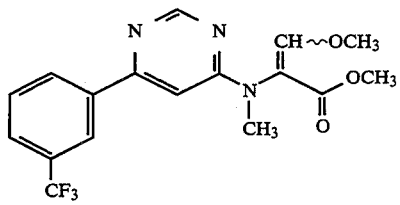

A mixture of 7.0 g (21.4 mmol) of methyl [N-methyl-N-[6-[(3-trifluoromethyl)phenyl]pyrimidin-4-yl]]aminoacetate, 100 m of toluene and 4.63 ml of a 30% strength sodium methanolate solution n methanol (25.8 mmol) is reacted for 5 hours at 70° C. under 50 bar of carbon monoxide.

The pressure is released, the batch is cooled to 5° C., and 5.3 g (42.0 mmol) of dimethyl sulphate are added dropwise with stirring. Stirring is continued at room temperature (approx. 12 hours), the mixture is treated with water and extracted using ethyl acetate, the organic phase is dried over anhydrous sodium sulphate, and the solvent is stripped off in vacuo, which gives a syrup which is purified by column chromatography on silica gel (eluent: dichloromethane/ethyl acetate 5:1).

80% of methyl 3-methoxy-2-[N-methyl-N-[6-[( difluoromethyl)phenyl]-pyrimidin-4-yl]amino-acrylate of melting point 105° to 108° C. are obtained.

TABLE 1

The following products are prepared analogously to Example 1

| | | Yield [%] | Melting point [°C.] |
|---|---|---|---|
| 2 | ![structure] | 81 | 126–129 |
| 3 | ![structure] | 72 | 135 |

TABLE 1-continued

The following products are prepared analogously to Example 1

| | | Yield [%] | Melting point [°C.] |
|---|---|---|---|
| 4 | 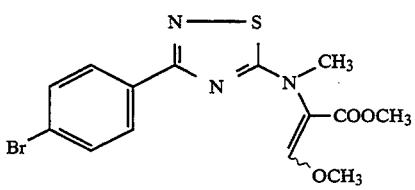 | 72 | 78–79 |

EXAMPLE 5

A mixture of 16.8 g (49.1 mmol) of methyl [N-[3-(4-bromo-phenyl)-1,2,4-thiadiazol-5-yl]-N-methyl]aminoacetate, 3.2 g of pulverulent sodium methylate (92.7%, 54.9 mmol) and 100 ml of toluene are reacted to constant pressure under 50 bar of carbon monoxide at 70° C. The pressure is released, and the residue is filtered off with suction, dried and subjected to ¹H NMR spectroscopy. It is identified as the sodium salt of methyl 2-[[N-[3-(4-bromo-phenyl)-1,2,4-thiadiazol-5-yl]-N-methyl-]amino]-3-hydroxyacrylate (77.8% of theory). 18.3% of the educt could be recovered from the filtrate.

The sodium salt is suspended in 50 ml of dimethylformamide, and 8.5 g (67.4 mmol) of dimethyl sulphate are added at 0° C. with stirring. Stirring was continued for a further approx. 2 hours at room temperature, the mixture was worked up, and 13.8 g (73.1%) of methyl 2-[[N-[3-(4-bromo-phenyl)-1,2,4-thiadiazol-5-yl]-N-methyl]amino]-3-methoxy-acrylate of melting point 91° C. are then obtained.

EXAMPLE 6

The procedure is analogous to Example 5, but 10.7 g of a 30% strength sodium methylate solution in methanol are employed instead of the pulverulent sodium methylate. The yield is 93.2%, and 3.8% of educt can be recovered.

COMPARISON TEST A (Compare Preparation Example 3)

10.3 g (0. 035 mol) of methyl N-[6-(4-chlorophenyl)2-pyridyl ]-N-methylaminoacetate and 50 g (1.2 mol) of methyl formate in 50 ml of dimethylformamide are added dropwise with stirring at room temperature to 2.4 g (0.1 tool) of sodium hydride in 60 ml of dimethylformamide, the mixture is then stirred for 3 days at room temperature, a further 0.5 g (0.021 mol) of sodium hydride and 10 g (0.24 tool) of methyl formate are added, the mixture is stirred for a further 5 hours at room temperature, another 0.5 g (0.021 mol) of sodium hydride and 10 g (0.24 mol) of methyl formate are then added, and mixture is stirred for a further 24 hours at room temperature.

After this, 14.0 g (0.11 mol) of dimethyl sulphate are added and the mixture is stirred at room temperature for a further 48 hours. For working-up, the reaction mixture is poured into water and extracted using ethyl acetate, the extract is dried over magnesium sulphate and concentrated in vacuo, and the residue is chromatographed on silica gel (eluent: dichloromethane/n-hexane 5:1).

This gives, as the 1st fraction, 7.1 g (69% of theory) of starting compound methyl N-[6-(4-chlorophenyl)-2-pyridyl]-N-methylaminoacetate and, as the 2nd fraction, 0.5 g (4.2% of theory) of the desired product methyl 2-[N-[6-(4-chlorophenyl)-2-pyridyl]-N-methylamino]-3-methoxyacrylate of melting point 120° C.

COMPARISON EXAMPLES B (compare Preparation Example 4)

A solution of 5.2 g (0.021 mol) of methyl N-(6-bromo-2-pyridyl)-N-methylaminoacetate and 30 g (0.72 mol) of methyl formate in 30 ml of dimethylformamide is added to a mixture of 1.2 g (0.05 mol ) of sodium hydride in 30 ml of dimethylformamide, the mixture is subsequently stirred for 15 hours at room temperature, 12.5 g (0.1 mol) of dimethyl sulphate are then added, the mixture is stirred for a further 15 hours at room temperature, then poured into water and extracted using ethyl acetate, the extract is dried over magnesium sulphate and concentrated in vacuo, and the residue is chromatographed on silica gel (eluent: dichloromethane/n-hexane 5:1).

This gives, as the 1st fraction: 1.5 g (29% of theory) of starting product methyl N-(6-bromo-2-pyridyl)-N-methylaminoacetate and, as the 2nd fraction: 1.8 g (30% of theory) of methyl 2-[N-( 6-bromo-2-pyridyl )-N-methylamino]-3-methoxyacrylate of melting point 78° to 79° C.

We claim:

1. A process for the preparation of a 3-alkoxyacrylate of the formula (I):

which comprises reacting a substituted acetate of the formula (II):

with carbon monoxide and a basic auxiliary in the presence of a diluent, thereby forming an intermediate of the formula (III):

and reacting such intermediate:
(a) with a dilute acid followed by extraction with an organic solvent, to isolate the free enol and then alkylating the enol with an alkylating agent in a diluent in the presence of a base at a temperature from 20° C. to 60° C., or
(b) reacting the enolate salt of the formula (III) with an alkylating agent directly in the reaction mixture, wherein in the above formulae (I), (II) and (III):
$R^1$ represents a pyridyl, which is optionally monosubstituted, the substituents being selected from the group consisting of phenyl, which is optionally substituted by fluorine, chlorine, bromine, methyl, ethyl, n- or i-propyl, n-, i-, s- or t-butyl, methoxy, ethoxy, n- or i-propoxy, methylthio, ethylthio, trifluoromethyl, trifluoromethoxy or trifluoromethylthio;

$R^2$ represents methyl, ethyl, n- or i-propyl, n-, i-, s- or t-butyl, or represents benzyl which is optionally monosubstituted to trisubstituted by identical or different substituents selected from the group consisting of fluorine, chlorine, bromine, cyano, nitro, methyl, ethyl, n- or i-propyl, n-, i-, s- or t-butyl, methoxy, ethoxy, n- or i-propoxy, methylthio, trifluoromethyl, trifluoromethoxy, difluoromethoxy, trifluoromethylthio, methoxycarbonyl, ethoxycarbonyl, methoximinomethyl, ethoximinomethyl, methoximinoethyl, ethoximinoethyl, cyclopentyl, cyclohexyl, and phenyl, benzyl, phenoxy or benzyloxy, each of which is optionally monosubstituted to trisubstituted in the phenyl moiety by identical or different substituents selected from the group consisting of fluorine, chlorine, bromine, methyl, ethyl, methoxy, ethoxy, methylthio, trifluoromethyl, difluoromethoxy, trifluoromethoxy and trifluoromethylthio;

$R^3$ represents methyl, ethyl, n- or i-propyl, or n-, i-, s- or t-butyl;

X represents oxygen, sulphur, $-CR^4R^5-$, or $-NR^6-$;

where
$R^4$, $R^5$ and $R^6$ independently of one another represent hydrogen, methyl, ethyl, n- or i-propyl, n-, i-, s- or t-butyl, or benzyl or phenyl, each of which is optionally monosubstituted to trisubstituted by identical or different substituents as set forth for $R^2$;

M⊕ represents hydrogen or the equivalent of an alkali metal cation or alkaline earth metal cation or ammonium cation; and n represents a number 0 or 1.

2. The process according to claim 1, wherein the reaction with carbon monoxide is carried out at a partial pressure of 1 to 200 bar.

3. The process according to claim 2, wherein the reaction with carbon monoxide is carried out at a temperature from 0° C. to 200° C. with the basic auxiliary present in from the stoichiometric amount up to a 35% excess.

4. The process according to claim 1, wherein the reaction with carbon monoxide is carried out at a temperature from 0° C. to 200° C.

5. The process according to claim 1, wherein the reaction with carbon monoxide is carried out with an excess of the basic auxiliary.

6. The process according to claim 1, wherein the reaction with carbon monoxide is carried out with the basic auxiliary present in from the stoichiometric amount up to a 35% excess.

* * * * *